United States Patent
Luotola et al.

(10) Patent No.: US 8,377,703 B2
(45) Date of Patent: Feb. 19, 2013

(54) METHOD AND DEVICE FOR DETECTION OF AN ANALYTE

(75) Inventors: Juhani Luotola, Espoo (FI); Antti Sunnari, Haukipudas (FI); Terho Kololuoma, Oulu (FI); Mikko Keränen, Tyrnävä (FI)

(73) Assignee: Orion Diagnostica Oy, Espoo (FI)

( * ) Notice: Subject to any disclaimer, the term of this patent is extended or adjusted under 35 U.S.C. 154(b) by 12 days.

(21) Appl. No.: 12/918,743

(22) PCT Filed: Feb. 20, 2009

(86) PCT No.: PCT/FI2009/000028
§ 371 (c)(1),
(2), (4) Date: Aug. 20, 2010

(87) PCT Pub. No.: WO2009/103843
PCT Pub. Date: Aug. 27, 2009

(65) Prior Publication Data
US 2010/0317123 A1 Dec. 16, 2010

Related U.S. Application Data

(60) Provisional application No. 61/030,747, filed on Feb. 22, 2008.

(51) Int. Cl.
*G01N 33/00* (2006.01)

(52) U.S. Cl. .......... 436/94; 436/164; 436/169; 436/170; 436/825; 422/110

(58) Field of Classification Search .................. None
See application file for complete search history.

(56) References Cited

U.S. PATENT DOCUMENTS

| 4,281,062 | A | 7/1981 | Kallis |
| 4,298,688 | A | 11/1981 | Kallies |
| 5,620,863 | A | 4/1997 | Tomasco et al. |
| 5,747,658 | A | 5/1998 | Veelaert et al. |
| 6,586,195 | B1 | 7/2003 | Friedman |

FOREIGN PATENT DOCUMENTS

| DE | 48717 B | 2/1965 |
| JP | 03039652 A | 7/1989 |
| WO | WO 95/12619 | 5/1995 |
| WO | WO 2006/122733 A2 | 11/2006 |
| WO | WO 2009/005884 A1 | 1/2009 |

OTHER PUBLICATIONS

Lemieux, R. U., et al. Spray Reagent for the detection of carbohydrates, 1954, Analytical Chemistry, vol. 26(5), pp. 920-921.*
Waffenschmidt et al., "Assay of Reducing Sugars in the Nanomole Range with 2,2'-Bicinchoninate," Anal. Biochem. 165:337-340, 1987.
International Search Report from International Application No. PCT/FI2009/000028, dated Aug. 17, 2009 (date of completion of search) and Aug. 26, 2009 (date of mailing of report).

(Continued)

*Primary Examiner* — Robert Xu
(74) *Attorney, Agent, or Firm* — Clark & Elbing LLP

(57) ABSTRACT

The present invention relates to a method, device and kit for analysing a sample for determining the presence or amount of an analyte, particularly carbohydrate, more particularly sugar, in the sample using a fabric.

8 Claims, 1 Drawing Sheet

OTHER PUBLICATIONS

Written Opinion from International Application No. PCT/FI2009/000028, dated Aug. 17, 2009 (date of completion of search) and Aug. 26, 2009 (date of mailing of report).

Examination Report from European Patent Application No. 09 713 393.8, dated Jun. 1, 2011.

Examination Report from GB0803401.9, dated Mar. 2, 2009.

\* cited by examiner

METHOD AND DEVICE FOR DETECTION OF AN ANALYTE

CROSS-REFERENCE TO RELATED APPLICATIONS

This application is the U.S. national stage filing under 35 U.S.C. §371 of international application PCT/FI2009/000028, filed Feb. 20, 2009, which claims benefit of U.S. Patent Application 61/030,747, filed Feb. 22, 2008.

FIELD OF THE INVENTION

The present invention relates to a method, device and kit for analysing a sample using a fabric for determining the presence or amount in the sample of an analyte, particularly a carbohydrate, more particularly sugar.

BACKGROUND OF THE INVENTION

Ambient hygiene receives increasing attention in laboratories, doctors' receptions, at home, in public facilities and industrial production plants. The trend is towards developing methods with which the person using or cleaning a space can quickly ensure its hygiene. Such methods should be extremely simple, user-friendly, rapid and inexpensive.

Hygiene can be ensured by determining the presence of microbes, such as bacterial concentrations or substances promoting bacterial growth, on the surfaces. Analysing microbes from surfaces using current methods is slow and requires professional expertise. An analysis of substances—e.g., sugars and proteins—facilitating microbial e.g. bacterial or fungi growth indicates the cleanliness of surfaces with almost comparable reliability.

There are quick and sensitive tests available for determining the presence of protein that are based on the reaction of bromine cresol green with proteins. Such tests were described in, e.g., patent application WO 2006/122733, which exhaustively discusses existing test formats based on the use of various membranes. The application also extensively discusses various methods for applying reagents to the membrane as roll-to-roll or other printing techniques.

Most of the known methods of analysis of carbohydrates such as sugars are based on methods in which sugars are indicated by colour change. Most methods based on colour change were developed for the spectrophotometric assay of sugars. To date, there are no inexpensive, rapid and easy tests available to determine the presence of sugars on surfaces. A problem related to sugars is their stable structure, which means that their analysis requires the presence of specific and likely unstable enzymes, incubation at elevated high temperatures, prolonged reaction times and/or chemicals hazardous to health or unsafe to be used.

There are several methods available for analysing sugars that are based on colour change. Methods based on the reduction of copper include Fehling's reagents, arsenomolybdate and the BCA (bicinchoninic acid) assay. Other methods applicable to sugar determination include the iron cyanide and DNS (dinitrosalicylic acid) methods, methods based on acetal formation, the anthrone method, indication methods including phenazine group, Schiff's reagent and tetrazolium blue, as well as boronic sensors based on circular dichroism, photoabsorption and fluoresence. Other methods applicable to determining sugars include enzymatic methods such as glucose-oxidase/perodixase and hexokinase, and luminescence methods including bioluminescence and chemiluminescence.

The available methods as such are not applicable for use in a test format where sugars are detected using a fabric method. All of the methods based on copper reduction require heating in order to effect the reaction sufficiently rapidly.

In U.S. Pat. No. 6,586,195, Janus Green B is used to indicate sugars. The patent demonstrates that reducing sugars are capable of reducing Janus Green B in sufficiently high concentrations, in the order of 10 g/l, in basic conditions, in which case Janus Green B changes from blue to grey. The colour change is not optimal since this reaction—a change from blue to grey—makes it very difficult to determine the result of the test with concentrations close to the detection limit.

Methods based on acetal formation and the anthrone method use strong acids in high concentration, which makes these methods unsuitable in the development of a fabric-based rapid test.

Indicator methods involve a simple reagent composition, which reduces the required volume of reagents to be printed onto the fabric. With sufficiently high sugar concentrations, changes in indicator colour can also be observed even at room temperature. The drawback is that only sugars with high reduction power, e.g. fructose, can be detected. There is also a lack of commercially available indicators.

Enzymatic and luminescence-based methods are sensitive and quick. The drawbacks associated with some enzymes include their cost and their unstable characteristics. Furthermore, the specific action of enzymes i.e. they act only on particular sugars precludes the use of such enzymes in rapid tests, which should be able to indicate a total level of all or almost all carbohydrates. Luminescence-based methods are viable only in connection with sugar-modifying enzymes and thus share the same problems as enzymatic methods.

Well-known methods familiar to experts in the field and the reagents they employ are not as such applicable for quick diagnostic methods. For example, the iron cyanide method is not suitable for quick analysis of sugars since in an acidic environment cyanide is released as hydrogen cyanide, a highly toxic substance. Some methods may not work at room temperature (e.g., the DNS method or Janus Green B), or they may have poor stability (e.g., enzyme-requiring methods, Schiff's reagent and acetal-forming reagents). Several methods also require highly acidic or alkaline conditions.

Accordingly, there is a need for a rapid and sensitive test for determination of carbohydrates on surfaces. Especially there is a need for a test which can be performed without an increase in temperature.

SUMMARY OF THE INVENTION

The present invention provides a method of determining the presence or amount of an analyte in a sample, said method comprising:
applying the sample to a fabric;
chemically modifying said analyte if present in the sample;
detecting the presence or amount of said chemically-modified analyte.

In one embodiment the means for chemically modifying the analyte, e.g. the reagent(s) are present on the fabric before the sample is applied to the fabric. Preferably the reagents are printed on or otherwise placed on, absorbed onto or attached to the fabric.

In one embodiment of the present invention the method further comprises inactivating an agent which interferes with the detection of chemically-modified analyte. Preferably the chemical modification and inactivation of interfering agent are carried out before detecting the chemically-modified analyte. According to this embodiment any sample or interfering product e.g. agent, reagent, composition or substance present in the sample, assay reagent applied to the fabric or formed during the assay procedure may be subject to inactivation for example by neutralization or by preventing its movement by precipitation. In one embodiment the means for inactivating the interfering agent is present on the fabric before the sample is applied to the fabric. These means are preferably printed on otherwise placed on, adsorbed onto or attached to the fabric. In one embodiment both the means for chemically modifying the analyte and the means for inactivating the interfering agent are present on the fabric before the sample is applied to the fabric.

The present invention also provides a test device suitable for carrying out the method, which device comprises a fabric carrying a means for chemically-modifying analyte, a means for detecting chemically-modified analyte agent and optionally a means for inactivating an interfering agent.

According to one embodiment said means are applied or printed serially e.g. as regions, zones or sections preferably such that when the device is used sample is able to travel through the regions in a sequential order.

The present invention further provides a kit for determination of the presence or amount of analyte in a sample, said kit comprising a test device comprising:
fabric material; and
means for modification of analyte by chemical modifying agents; and
means for inactivation of interfering reagents; and
means for detecting chemically-modified analyte.

Furthermore, the present invention relates to a roll-to-roll printing method, wherein the reagents and said means are printed sequentially on specified areas on a fabric.

In one embodiment the analyte is a carbohydrate. In one embodiment the carbohydrate is a sugar. Preferably the sugar comprises fructose, dextrine, lactose, maltose and/or sucrose.

The present invention provides a method of determining sugar in a sample comprising a non-enzymatic method performed at room temperature by applying said sample to a fabric.

DETAILED DESCRIPTION OF THE INVENTION

Figure 1:
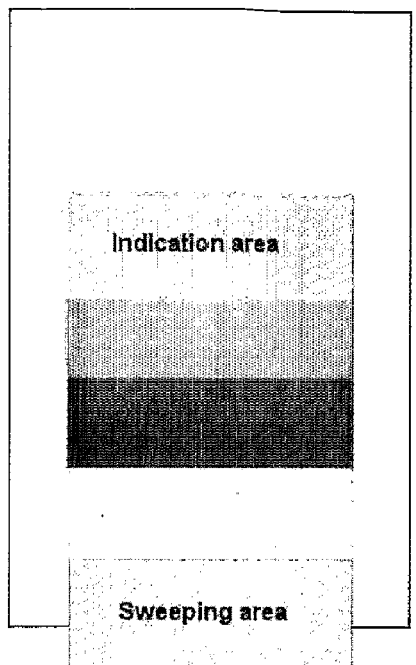
FIG. 1. Structural principle of the moisture-absorbing fabric method.

This invention relates to a method, device and kit for analysing a sample in such a manner that the analyte in the sample can be chemically remolded or modified and optionally interfering reagents or agents and/or products formed during the assay can be inactivated during the assay.

The method is broadly applicable to the measurement of an analyte which is stable or otherwise difficult to measure in the form in which it is found in a sample. The method of the present invention is particularly suitable for determining the presence of carbohydrates, particularly sugars, in a sample. The invention relates to the detection of sugars in the sample using a moisture-absorbing fabric method. The method may be carried out without increasing the reaction temperature. The present invention also relates to a fabric-containing device for use in the method. In manufacturing the device, chemicals used in the assay may be transferred onto the fabric using conventional printing methods. A suitable method of manufacture is disclosed in detail in WO 2006/122733 incorporated herein by reference. Lamination of the fabric between plastic membranes allows the liquid to move rapidly along the fabric. However, the manufacturing procedure is distinct from the procedure disclosed in WO 2006/122733 by being more complicated and challenging due to clearly distinct areas to which the remolding agent(s), inactivating agent(s) and typical assay reagents are applied. The method and device of the present invention are applicable as a rapid test. The basic requirements for a rapid test are simplicity, sensitivity, specificity, safety, ease of use, disposability and suitability for industrial production with printing methods.

Although the test of the present invention may be applied to any suitable analyte, for convenience the following description will discuss in detail the embodiment in which the analyte is a carbohydrate. The test of the present invention may be used to determine carbohydrates, particularly sugars, such as fructose (fruit sugar), dextrin, lactose (milk sugar), maltose (malt sugar), and sucrose (granulated sugar) preferably using a visual colour change. When exploiting traditional methods, fructose is the easiest to determine whereas sucrose and starch are the most difficult. Sucrose and starch are the most difficult to determine since they have a much lower reducing power than the other above-mentioned sugars. The present invention is able to detect the presence of 150 μg sugars, including the presence of neutral sugars such as sucrose.

To assess hygiene, indication tests are mainly qualitative in nature, indicating the presence of a sugar in the sample within a given sensitivity range. The present invention is able to indicate the presence of carbohydrates, particularly sugars, to a sensitivity such that the detection limit is 1 g/l. This corresponds to an ability to detect 500 μg of sugars in a 500 μl sample taken from a 10×10 $cm^2$ surface. The detection limit for sugars (using the same units) is preferably 0.5 g/l, (250 μg) more preferably 0.2 g/l (100 μg), 0.1 g/l (50 μg), 0.05 g/l (25 μg), 0.02 g/l (10 μg) or 0.01 g/l (5 μg).

The present invention enables a simple and low-cost device for determining hygiene in e.g. hospitals, doctor's offices, laboratories, food industry, dairies, bakeries, breweries and beverage industry.

A "carbohydrate" is a chemical compound which contains carbon, oxygen and hydrogen. It is preferably a sugar.

A "sugar" is a water-soluble mono-saccharide, oligo saccharide or poly saccharide.

A serial reaction on a fabric may be used to carry out the method of the invention. Briefly, the sample is introduced to the fabric to react with desired chemicals in a specific predetermined order.

The sample is typically introduced to the fabric by wiping the fabric over a surface to be tested. Other embodiments are also envisaged. For example, the fabric may be placed on a surface to be tested or a liquid sample may be removed from a test area and introduced into the fabric using e.g. a pipette or similar transferring means. The surface and/or the fabric may be treated before they are brought into contact. For example, one of them (preferably the surface) may be wetted with an aqueous solution to assist in providing a fluidic sample. The aqueous solution may be applied as e.g. a spray or wash. This is particularly desirable if the surface to be tested is dry or does not itself carry sufficient moisture to create an adequate fluid sample. The aqueous solution is typically water or a solution comprising materials beneficial in the carrying out of the assay, e.g. a buffer.

A buffer should not contain compounds which interfere with the chemistry used to modify the analyte or to detect the modified analyte. For example, when the analyte is a carbohydrate the chemical modification is typically an oxidation and the detection step typically involves the use of metal complexes whose colour is a visible indication of a positive result. In this embodiment interfering reagents which should preferably be absent from the aqueous solution comprise but are not limited to iodates and phosphates which form complexes with copper, and boric acid and borates which form complexes with carbohydrates interfering with the oxidation. Buffer solutions can contain primary, secondary and tertiary alcohols although di, tri etc. polyalcohols are not preferred. The aqueous solution can also contain iodine and stabilizers, such as KI, for the detection of starch or other polysaccharides whose movement in the test device may be more limited due to the chromatographic separation.

Suitable aqueous solutions are buffers which are prepared according to ACS or ProAnalysis grade. The aqueous solution should also have a low content of metal cation impurities. Preferably it has not more than 0.002% or not more than 0.001% Fe. Preferably it has not more than 10 ppm, or not more than 5 ppm of heavy metals such as Pb. More preferably the content of metal cation impurities of the aqueous solution is as low as possible.

Once the fluid sample is introduced to the fabric, typically the first step is to chemically modify the carbohydrate. When the carbohydrate is a sugar it is preferably remolded or modified in a manner which enables determination at room temperature. In one embodiment the sugars are made more reactive by opening the ether linkage in the sugar ring structure and between monomers, followed by an oxidizing process, wherein the number of aldehyde groups is increased. The means for chemically modifying the carbohydrate may be a reagent, for example, periodic acid or a periodate salt such as sodium periodate or another type of chemical compound such as a cerium(IV) salt. Such a chemical modifying means is preferably an oxidizing agent with sufficient oxidation potential to cleave the carbohydrate chain between two hydroxyl groups, and is preferably colorless.

Other reactions contemplated for the modifying of carbohydrate into a more easily detectable form and which can be used as a basis for a method and test device of the present invention include but are not limited to:

Mutarotation, where —OH group is mutarotated from α- to to β-form with weak acid.

Acid catalyzed formation of oxygen bridge (ether) between sugar —OH and alcohol.

Formation of carboxylic acid, for example gluconic acid, with the presence of weak oxidizer, for example $Cu^{2+}$.

Formation of dicarboxylic acid, for example glucoronic acid, at an elevated temperature with strong acid.

Reduction with $NaBH_4$ to sugar alcohols (breakage of ether ring and formation of hydroxyl end group).

Formation of acetates when Na-acetate and acetic anhydride exist.

Formation of aldehydes with the presence of, for example, silver oxide and methyl iodide It is believed that the method of chemically modifying an analyte before detecting the chemically-modified analyte is a procedure not previously used on fabrics. In the method of the invention, sample and modifying or remolding means should meet, preferably interfering agents should be inactivated and only desired compositions or substances should move further in the fabric material.

An "interfering agent" is a substance which, if present when the chemically-modified analyte is detected, would interfere with the detection of the chemically-modified analyte. The interfering agent may be present in the sample originally, it may be superfluous reagent from the chemical modification of the analyte or it may exist as a result of the reaction to chemically modify the analyte e.g. a product or by-product of the reaction.

When the analyte is a carbohydrate, examples of interfering agents include iodates and phosphates which form complexes with copper as well as boric acid and borates which tends to form complexes with carbohydrates interfering with the oxidation of a carbohydrate. Also, reducing agents such as metal cations are capable of reducing copper thus leading to a colored reaction without sugar.

An interfering agent may be inactivated either in the same region of the fabric as the chemical modification takes place or in a subsequent region of the fabric through which the sample comprising the chemically-modified analyte passes. Preferably the inactivation takes place in a subsequent region. The inactivation takes place before the chemically-modified analyte is detected.

The chemically-modified analyte is then detected. When the analyte is a carbohydrate, the detection is preferably carried out using a BCA assay. In a BCA method $Cu^{2+}$ oxidizes sugar under alkaline boiling. Tartratic acid is used as a complexer for $Cu^{2+}$ preventing the formation of copper hydroxide precipitation. During this process $Cu^{2+}$ is reduced to $Cu^+$ which reacts with bicinchoninic acid and forms a coloured complex which formation is attributed to the existence of sugar.

While the BCA method uses incubation, even minute amounts of reduced copper are detectable as a BCA complex, and the reagents used may be brought to solidify into stable compounds on the fabric.

The fabric is preferably a synthetic fabric as fabrics based on e.g. natural cellulose and viscose tend to produce false positives when used to detect a carbohydrate. Synthetic fabrics which may be used include but are not limited to cellulose-and viscose-free fabrics, polyester fabrics, poly ethane, polyamide fabrics, polypropylene fabrics, polyvinylchloride fabrics and their combinations. In one embodiment the fabric is a polyester fabric.

The term "fabric" is used in the present disclosure and defined to include any material such as that as which is capable to absorb a fluidic sample and transport or carry said sample by capillary action. A commonly used term is "matrix" which is a material with corresponding features.

The term "modify" is used and defined to mean also remolding.

The term "region" is used and defined to mean also "zone", "phase", "area", "section" e.g. a multi-step test.

The term "wiping" is used and defined to mean also "sweeping". During wiping the fabric absorbs fluid from surface.

The term "product" is used and defined to mean any agent, reagent, composition or substance.

In one embodiment of the present invention, the BCA method is applied to function on a fabric. In producing a suitable device a chemical in liquid form is printed on the fabric where it dries. In solid form the chemical does neither move along the fabric nor is diluted via evaporation and its stability improves compared with its stability in the liquid form. The quick diagnostic test of the present invention enables detection of sugars on surfaces based on a reaction causing a colour change which eliminates the deficiencies described as problems associated with the above-mentioned tests. The test device of the present invention is disposable and may be manufactured using a roll-to-roll printing method, which keeps the cost low. Carrying out the test is easy and does not require special training. Furthermore, the chemicals included are safe for everyday use.

There are several methods available for determining and indicating sugars; these tests were discussed in the above introduction. Methods found in literature include BCA and various indicators. These methods satisfy one of the preferred requirements for the success of the test, i.e. they cause a colour change at room temperature. The drawback is that they require high sugar concentrations, although minute amounts may be indicated by thermocatalysis. However, the properties discussed in the literature are not sufficient for the methods to be directly usable with fabrics. The present invention eliminates these problems and the need for heating, yet the test is sensitive enough to determine even low sugar concentrations. The present invention enables test tube method conditions to be created on a fabric, which causes the sample transferred from the moistened surface to the fabric to undergo a colour change if the sample includes sugar.

According to the invention, the reagents used in the studied methods were transferred to the fabric by printing, which in addition to cost effective manufacturing of the test device also ensures homogenous reagent concentrations throughout the print area. The most common roll-to-roll printing methods include relief printing, gravure printing, offset printing and serigraphy, as well as ink-jet in some applications.

Gavure printing is preferred as the printing method for this invention. However, it will be clear to those skilled in the art that other printing methods may also be used with slight modifications. Gavure printing is preferred because of the simple mechanics of ink transfer, which allows the use of inks with significantly different rheological properties, and the good chemical transfer and chemical resistance properties of the method. In the examples printing was done with a table-top test printing press.

Testing the moisture-absorbing fabric involved applying a sugar containing liquid sample to a clean surface in sufficient amounts. The edge of the fabric was held in contact with the sample until the sample liquid reached the indication area.

All methods were tested with the following sugars: fructose, dextrin, lactose, maltose and sucrose of which sucrose is neutral rather than a reducing sugar.

EXAMPLE 1

Both biological and synthetic fabrics were tested. In an early stage it was noticed that biological fabrics containing cellulose and viscose and hence sugar-like groups were unsuitable to be used because sugar-like functionalities caused also a zero sample to change the color of the test. Therefore, synthetic cellulose and viscose-free fabrics were also tested and colour change with a zero sample was not observed. From tested synthetic fabrics it was found that polyester fabrics are favoured over polypropane due to its less hydrophobic nature.

Waffenschmidt or Smith protocols used during experiments for the determination of sugars are as follows (Smith et al., Measurement of Protein Using Bicinchoninic Acid, 1985, 150, 76-85; Waffenschmidt et al., Anal. Biochem. 1987, 165, 337-340).

Waffenschmidt et al. protocol for determination of reducing sugars with BCA-method:
Solution compositions
Solution A
BCA 971 mg
$Na_2CO_3 \times H_2O$ 31.75 g
$NaHCO_3$ 12.1 g
ad. $H_2O$ 500 ml
Solution B
$CuSO_2 \times 5H_2O$ 624 mg
L-serine 631 mg
ad. $H_2O$ 500 ml
Solutions are mixed 1:1 daily.

Sugar sample is mixed with 1 ml mixture of A and B solution. This sugar containing mixture is kept for 15 minutes in 100° C. heating block. After cooling to room temperature, about 20 minutes, absorption is recorded at 560 nm.

Detection limit for reducing monosaccharides is about 5 nmol. For glucose 5 nmol is about 0.9 μg.

Solution compositions used during Smith et al. protocol for determination of proteins with BCA-method are shown in Table 3.1:

TABLE 3.1

Solution compositions in the BCA mix.

| Solution A | | Solution B | |
|---|---|---|---|
| Chemical | Quantity | Chemical | Quantity |
| Sodium salt in BCA | 1 g | $CuSO_4 \times 5H_2O$ | 4 g |
| $Na_2CO_3 \times H_2O$ | 2 g | $H_2O$ | ad. 100 ml |
| Disodium tartrate | 0.16 g | — | — |
| NaOH | 0.4 g | — | — |
| $NaHCO_3$ | 0.95 g | — | — |
| $H_2O$ | ad. 100 ml | — | — |
| pH adjusted, 10 M NaOH, to 11.25 | | — | — |

A and B solutions are mixed in proportion to 50:1 daily.

Sample solution and mixture of A and B solution are mixed in proportion to 1:20 respectively. Mixture is incubated if time limit for determination is narrow or only minute amounts of protein persist.

The absorbance was measured using a spectrophotometer. Same absorbance reading is achieved when different time and incubating temperatures are used. This is presented in table 3.2.

TABLE 3.2

Achieving 0.2 absorbance by different protein amounts and incubating parameters.

| Absorbance | Protein amount | Incubating temperature | Incubating time in minutes |
|---|---|---|---|
| ~0.2 | 20 μg | Room temperature | ~5 |
| ~0.2 | 20 μg | 37° C. | ~2.5 |
| ~0.2 | 5 μg | 60° C. | ~3 |

Despite that Smiths protocol is meant for protein analysis it can be used for determination of reducing sugars. This is shown in Table 3.3, where the interfering effect of reducing sugar (glucose) is presented.

TABLE 3.3

The effect of reducing sugar in Smith protocol

| 100 μl sample consisting 50 μg of BSA* and | BCA assay** (BSA* found) when water blank correction was used. | BCA assay** (BSA* found) when interference blank correction was used. |
|---|---|---|
| 900 μg glucose | 245 μg | 57.1 μg |
| 450 μg glucose | 144 μg | 47.7 μg |
| 90 μg glucose | 70 μg | 49.1 μg |

*Bovine serum album (protein).
**Protocol described earlier with 37° C. incubating for 30 minutes.

In "water blank correction" all of the reagents exist in blank+same amount of pure water as in sample size to maintain volume of sample and blank same. Blank absorption is recorded and absorption amount is subtracted from sample absorption to correct absorption caused by contamination, reagents, lab ware, etc.

"Interference blank correction" is similar to "water blank correction", but blank also comprises the same amount of interfering agent(s) as in sample.

Accordingly, absorption caused by interfering agent, contamination, reagents, lab ware etc. can be subtracted from sample.

The compositions of the BCA reagents used in experiments according to Smith protocol are listed in Table 3.1. In test tube methods, reagents were mixed in the ratio 50A:1B, besides which the sample was incubated.

Chemicals used in the BCA method were transferred onto the plain and different buffer washed fabrics using the table-top test printing press. A range of different fabrics, pH values and combinations of BCA chemicals were tested creating the basis for the further development work. The test observations and their explanations are listed in Table 3.4.

TABLE 3.4

Test observations and their explanations

| Observation | Explanation |
|---|---|
| The intensity of the zero reaction increased with higher pH values. | A biological fabric was used in the test; thus a more intense reaction was acquired when approaching the optimal conditions of the BCA method. The optimal pH value for sugars when using the BCA method is 10.2. |
| Biological fabric caused a zero reaction and zero reactions were not observed with synthetic fabrics. | The zero reaction observed with biological fabrics was caused by copper reacting with the reducing substances present in the biological fabrics in the form of viscose and cellulose. The lack of zero reaction with synthetic fabrics confirmed the hypothesis. |
| When high-pH phosphate buffers were used, the zero reaction was colourful, although the colour faded gradually. The lowest detection limit was achieved with a sodium acetate buffer with a pH value of 4.7. | When phosphate buffers were used, the colour reaction occurred, but the colour faded gradually. This was due to the copper reacting with phosphates. An acetate buffer with a pH value of 4.7 was the most sensitive since the test was performed using a buffer and substrate that did not interfere with the BCA method |

The BCA method was developed further with the aim of creating the optimal conditions of the test tube method on the fabric. Since biological fabric was shown to be unsuitable due to positive result in the negative control reaction polyester fabric was chosen as the substrate since it is free of the reducing groups that caused the false control reaction.

In order to study the impact of the buffer and pH, the fabric was washed with 0.1 M carbonate buffer, pH 10.2, and the results were compared with the acetate buffer, pH 4.7. BCA reagent solutions were printed on fabrics washed with a sodium carbonate buffer in the ratio A+½B, i.e. solution B was diluted to half strength with water before printing. Solution A was printed first; once the print was dry, the ½B solution was added. Table 3.1 lists the solution compositions before diluting.

In earlier tests the detection limit for fructose on fabrics washed with a sodium acetate buffer, pH 4,7, was 5 g/l. Other tested sugars failed to cause a colour change. A carbonate buffer with a pH of 10.2 lowered the fructose detection limit to 1 g/l, while other sugars still failed to cause a colour change.

As a test tube method analysis involves sample incubation, the impact of heat on the fabric method was tested by placing fabrics moistened with sugars into an oven at 80° C. for 30 minutes. The thermal effect was also evident with the fabrics; the detection limit with fructose was 0.05 g/l, but a colour change reaction was not observed with other sugars.

Since a copper complexing agent is an element of the method, various complexing agents were tested to try to improve the performance of the test. In previous tests sodium tartrate acid was used as the complexing agent of $Cu^{2+}$, but it was now replaced with L-serine as Waffenschmidt had discovered L-serine to be a more efficient complexing agent for copper than sodium tartrate acid.

The following test was based on Waffenschmidt's reagent compositions (Waffenschmidt et al., Supra). The fabrics were treated with the same carbonate buffer and the chemicals were printed on the fabrics in the same manner as in the earlier tests. Two different reagent ratios, A+B and A+½B, were used in the printing. Table 3.5 shows the compositions of solutions A and B.

TABLE 3.5

Composition of Waffenschmidt's BCA solutions.

| Solution A | | Solution B | |
|---|---|---|---|
| Chemical | Quantity | Chemical | Quantity |
| BCA | 0.194 g | $CuSO_4 \times 5H_2O$ | 0.194 g |
| $NaCO_3 \times H_2O$ | 6.35 g | L-serine | 0.126 g |
| $NaHCO_3$ | 2.42 g | $H_2O$ | ad 100 ml |
| $H_2O$ | ad. 100 ml | — | — |

When sugars were tested on fabrics, the zero reaction with water was intense and the fabrics spontaneously turned violet within two weeks. It is believed that L-serine complexed $Cu^{2+}$ and gradually reduced it to Cu, which was followed by the formation of a strong-coloured BCA copper complex. Therefore, Smith protocol seem to be favored over Waffenschmidt protocol to be used in further development work.

Based on the above tests, it was realized that the correct pH value, buffer solution and complexing agent did not give the method a sufficient degree of sensitivity. A suitable catalyst to improve the detection of sugars with the BCA method could not be identified based on the literature.

The oxidizing power of copper plays a role in the BCA method. Thus, and based on the results and conclusions presented above, an attempt was made to find a more powerful oxidizing agent than copper. According to the invention, it would be possible to detect the reduction of the oxidizing agent using a suitable colour-changing indicator.

However, adopting a more potent oxidizing agent gave rise to several problems. As the oxidizing power of a substance increases, its toxicity and reactivity to other substances also increase. Reactivity causes several substances to decay or reduce spontaneously, weakening the stability and function of the test.

We then realized that one could modify or remold the sugars themselves in a way that would make them more easily detectable using methods based on colour changes. Accordingly, we attempted oxidating the sugars with the aim of increasing the number of aldehyde groups they contain since it is the aldehyde groups in particular that react with copper in methods based on copper reduction.

Three chemicals suitable for oxidizing sugars were identified from the literature: periodic acid, sodium periodate and Dess-Martin periodate, which oxidise sugars in ways that increase aldehyde groups. As described below we found that increasing the number of aldehyde groups lowered the detection limit of the method and made it possible to detect also sugars with low reduction power and neutral sugars.

EXAMPLE 2

In the test tube method sugar, sodium periodate and the BCA reagents listed in Table 3.1 were added to a test tube in given order. The sugar-containing test tubes changed colour at room temperature within five minutes but the zero reaction (negative control) occurred five minutes later. The test demonstrated a significant progress since the BCA method was now functional at room temperature and even neutral sugars caused a colour change. The zero reaction was attributed to the sodium tartrate contained in the BCA reagent.

The effect of sodium tartrate was studied by preparing the solution A in the BCA mix shown in Table 3.1 without sodium tartrate. All sugars failed to cause a colour change in the test tube method. This may be attributable to the oxidizing effect of sodium periodate, in which case the copper is reduced by the sugars but re-oxidised by the sodium periodate ($Cu^+ \rightarrow Cu^{2+}$).

A decision was made to test sodium periodate as part of the BCA method with fabrics. The BCA reagents were printed on the fabrics in the same way as in previous tests and sodium periodate was added last. The aim was to establish a clear time limit between the negative control sample and the sugar-containing sample.

Based on the results, it was concluded that sodium periodate can be used to enhance the sensitivity of the test but sodium periodate also interferes with the method so that the sugar-induced colour change may only be observed in fabric after 30-40 minutes. Therefore, methods to neutralize and/or inactivate sodium periodate after the remolding or modifying of sugar was needed.

EXAMPLE 3

Our preliminary results and our inventive problem-solving led us to adopt a multi-step test comprising chemicals which react as in a series i.e. multi-region or multi-zone test. Capillary action makes the sample solution flow in the fabric where it reacts with the printed chemicals on specific areas on the fabric.

In the test concept, sugar impurities on the investigated surface were carried through the moisture-absorbing fabric containing the necessary chemicals. In the fabric, the sugars in the liquid sample react with the chemicals in a given order. Thus even reactive chemicals that would usually inhibit the reaction or cause a zero reaction, such as those described in Example 2, can be used as reagents since they can be inactivated before BCA-analyte indication area. Accordingly, the reagents used in said test tube method can be used on fabric material in a rapid multi-step test when the molding and inactivation of the present invention is exploited.

In the earlier test tube method, sodium periodate was found to facilitate the BCA method at room temperature. The problem was the occurrence of a positive test result with a negative sample a few minutes later and the difficulty in getting the method to function with fabrics. We realised that the method could be improved by including additional steps.

It is known that the ring structures of the sugars and the linkages between monomers involve an ether linkage. Opening this ether linkage accelerates the reaction of sugar with sodium periodate and further with copper. Halogen acids, hydrogen iodide and hydrogen bromide, or low pH, may be used to break ether linkages (Clayden et al., Organic Chemistry, OUP 201, p. 434). Hydrogen halides cannot be used directly as they cannot be fixed on a fabric in solid form.

The ether linkages of sugars were broken in acidic conditions, which were achieved in test tube method tests using sulphuric acid. Next, sugars were oxidised with sodium periodate and the excess sodium periodate was neutralised with sodium thiosulphate. The solution was neutralised with sodium hydroxide before adding the BCA reagents. Stoichiometric ratios were used as the starting point for optimising chemical concentrations, resulting in the concentrations shown in Table 4.1.

TABLE 4.1

Reagent rations in the sodium periodate/thiosulphate method.

| Reagent | Volume |
|---|---|
| Sugar solution 1 g/l | 200 µl |
| Suplhuric acid 0.1 M | 100 µl |
| Sodium periodate 11.3 g/l | 100 µl |
| Sodium thiosulphate x 5H2O 11.6 g/l | 120 µl |
| NaOH 0.1 M | 200 µl |
| BCA solution B, diluted to 5% | 100 µl |
| BCA solution A containing tartrate acid | 500 µl |

The above-described method caused a colour change with sucrose and the zero sample (negative control) changed colour 24 minutes later in a test tube method test.

According to our inventive insight the reactivity of sugars may be increased in a multi-step process and the reagents interfering with their determination may be inactivated, prior to indication of analyte in sample.

During the development of the fabric test the chemicals were printed on fabrics that were then cut into strips. The strips were placed side by side, forming a structure similar to a continuous fabric, and laminated between plastic membranes. The initial choice fell on cellulose acetate plastic; however, its hydrophilic nature made the liquid move at the plastic-fabric interface. The problem was resolved by using hydrophobic plastic, which retained the sample liquid in the fabric. FIG. 1 depicts an example of a structure of the moisture-absorbing fabric method. There may be different regions of the fabric containing different reagents. The different colours in FIG. 1 depict potential reagent areas.

Accordingly, a test device is provided which comprises a fabric material, wherein the fabric comprises either a set of distinct strips combined together in series to form a continuous fabric or one single fabric. Each of the distinct strips comprises at least one reagent, preferably only one reagent, whereas the one single fabric comprises more than one reagent provided on the fabric in a predetermined and consecutive order. Said fabric material is laminated by two impermeable layers, one of the impermeable layers having at least one opening, preferably a plurality of openings. The shape of the openings may be round, triangular, rectangular, square formed or anything alike. The size of the openings may vary from perforations of 0.01 mm to more than 2 cm, whereas the size of one single opening may exceed 2 cm. In order to facilitate the, usually, capillary transport of fluid in the fabric material the impermeable member is typically made of hydrophobic material. Suitable materials include a non-woven polypropylene material.

The device may also provide a format comprising at least one sampling opening followed by a passage comprising a series of reagent zones laminated with said impermeable, either transparent or non-transparent, layer which end in at least one non-laminated opening or a transparent lamination layer comprising the test indication region.

Obviously, the wiping or absorbing test device may have any form which is able to exploit the principle of the invention e.g. to modify the sample to be tested and inactivate interfering reagents. For example different formats having test indication region on either side of the device, e.g. on the same or opposite side of the sample wiping or absorption area may be possible.

As described the invention relates preferably to a one layer fabric e.g. lateral flow test format comprising reagents applied sequentially in different zones. It is evident for those skilled in the art that such lateral flow tests may comprise various designs and technical and methodological approaches.

Optionally the device may also comprise a layer of fabric material which allows the sample to pass through whilst limiting backflow of reagents or sample. Said layer is often also called a semi-permeable layer. For example, the semi-permeable layer may be made of a hydrophobic material. A suitable hydrophobic material is a non-woven polypropylene material.

The sodium periodate-sodium thiosulphate method used in the test tube method was transferred to the fabric by printing each reagent on a separate fabric with the table-top test printing press. The aim of the multi-step test is to break the sugar rings in acidic conditions and oxidise the sugar chain with sodium periodate into shorter carbon chains containing a reducing aldehyde group. The excess sodium periodate, which interferes with the BCA method, is neutralised with sodium thiosulphate prior to indication and the resulting carbon chains containing an aldehyde group chain reduce the copper and a strongly absorptive complex is formed.

The fabric used was polyester fabric, which was pretreated with 0.1 M carbonate buffer with a pH of 10.2. The BCA reagents were printed on this pretreated fabric in the ratio A+½B. Other reagents were printed on untreated fabrics.

It is preferred not to use the method involving sodium thiosulphate, which neutralises sodium periodate, on the fabric since small amounts of excess sodium thiosulphate during the tests may cause a zero reaction. In addition, the detection limit with this method is high; sugar solutions with concentrations below 1 g/l failed to cause a visual colour change. It is preferred to use ferrous sulphate in place of the sodium thiosulphate. The ferrous sulphate reduces periodate into iodate, simultaneously oxidizing into trivalent ferric ion.

Iron(II)sulphate (FeSO$_4$×7 H$_2$O) with a concentration of 72 g/l, sodium periodate with a concentration of 11.3 g/l, sulphuric acid with a concentration of 0.1 M and BCA reagents A+½B were printed on separate fabrics. They were laminated into a single structure so that sulphuric acid was first, followed by sodium periodate and finally ferrous sulphate. This was followed by a clean strip of fabric as the reaction area and then the BCA reagents. As the sample moves along the fabric, the reaction series shown below is expected to happen (Waffenschmidt et al., Supra; Clayden et al., Organic Chemistry, OLIP 2001, 146, 344, 1369; Caldwell et al., J. Biol. Chem. 1938, 123, 595-606).

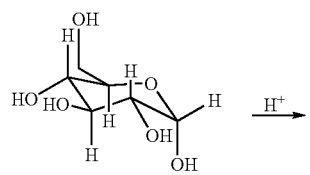

Acid catalyzed sugar ring opening

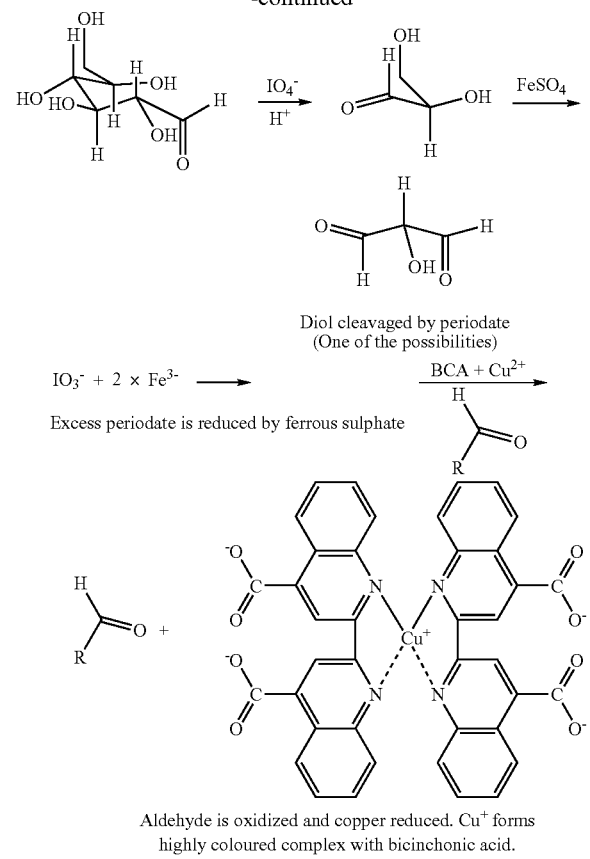

Presumed reaction series on a fabric.

In the first phase ring structures are opened with a sulphuric acid. In the next phase periodate cleave diols and oxidizes sugars to aldehydes. Periodate is neutralized with ferrous sulphate and in the final phase copper is reduced by formed aldehydes followed by the colored complex formation with BCA.

As the sample moves along the fabric, ferrous sulphide was found to be carried until the indication area and cause a false positive reaction. This was due to the bivalent iron reacting with copper, resulting in iron oxidation and copper reduction; $Fe^{2+}+Cu^{2+}\rightarrow Fe^{3+}+Cu^{+}$. Ferrous sulphate should be present in the correct amount in order to be completely oxidised by sodium periodate and not to cause a zero reaction. While trivalent iron no longer reacts with copper, its being carried to the indication area nevertheless weakens the detection limit since its reddish brown colour may cover the violet colour of the BCA copper complex formed.

A carbonate buffer zone was introduced to prevent iron from being carried into the indication area. The fabric was washed with 0.1 M carbonate buffer, pH 10.2, and dried in an oven at 60 degrees centigrade. The carbonate layer was placed after the ferrous sulphate and before the indication area. The iron reacts with the carbonate ions and hydroxide ions in the alkaline carbonate layer, forming the compounds shown below (Smith et al., Supra).

$Fe^{2+}+CO_3^{2-}\rightarrow FeCO_3$ $Fe^{2+}+2\ OH^-\rightarrow Fe(OH)_2$ $Fe^{3+}+3\ OH^-\rightarrow Fe(OH)_3$ Instead of being soluble, the presented iron compounds precipitate, which stops the movement of the accumulating compound on the fabric.

The resulting test was functional and a response was obtained with sugar-containing samples whereas the negative control sample remained colourless. The detection limit of the method was 0.5 g/l. An example of a functional test conception of sugar test on a fabric is presented in FIG. 2 comprising: 1. Sweeping area 2. Sulphuric acid 3. Sodium periodate 4. Ferrous sulphate 5. Carbonate buffer and 6. BCA, A+½B. It should be noted that sodium periodate and sulphuric acid layers can be substituted by periodic acid.

The method as disclosed in the present invention typically comprises printing the chemicals side by side on one fabric, or separately on different fabrics, which are further laminated side by side to form a continuous fabric structure. These layers were viable during the development of the test since it was compiled of separate strips of fabric. However, it is envisaged that a continous piece of fabric will be used in roll-to-roll mass production, which will make it difficult in practice to wash parts of the fabric with the carbonate buffer. Therefore, the required amount of the carbonate buffer has to be transferrable by printing. A unimolar carbonate buffer was printed in the indication area. The amount of the carbonate buffer on the fabric in the area where iron is precipitated was increased by increasing the molarity of the carbonate buffer solution eg. saturated solution with a pH of 10.2. Solution was printed twice on a fabric using a printing cylinder capable of transferring 24,9 ml/m$^2$. In the printed area the iron precipitates as carbonate and its movement with the sample liquid is prevented, thus eliminating the need to optimize the quantity of the ferrous sulphate. By adjusting the molarity of the buffer solution and by changing the mesh size and cup depth in the printing cylinder the amount of reagent to be transferred can be controlled.

As earlier described, the amount of chemicals may be furthermore reduced by replacing sodium periodate with orthoperiodic acid $H_5IO_6$ ($HIO_4 \times 2 H2O$) (Masuda et al, J. Org. Chem. 1994, 59, 5550-5555). Orthoperiodic acid is available in solid form and remained stable on the fabric. The pKA value of orthoperiodic acid is 1.64; thus it also replaces weak sulphuric acid in breaking sugar rings.

In order to enhance the sensitivity of the test, the ratio of BCA reagents on the fabric was further optimised. In test tube methods solutions A and B were mixed together in the proportion of 50:1. Significantly higher ratios of 1:1 (A+B) and 2:1 (A+½B) were used when printing the reagents on the fabric, in which case the blue colour of the copper interfered with the observation of the violet BCA complex. The copper solution was diluted to 1:10 (¹⁄₁₀B) with water. Redaction of the amount of copper lowered the detection limit and the colour change of a 0.1 g/l sugar solution could be detected instead of the 0.5 g/l sugar solution used previously.

EXAMPLE 4

In one embodiment the test device for sugar detection at room temperature contained five different regions and five different chemicals and/or reagent liquids printed on these areas. As a first area there is a sweeping or suction area that does not contain any chemicals. After that liquid sample moves to an area containing printed orthoperiodic acid where ether linkages in sugar ring structures and between monomers are broken. Furthermore, sugars are oxidized to aldehydes in this area by the orthoperiodic acid. The next area contains the ferrous sulphate which reduces periodate into iodate, simultaneously oxidizing into trivalent ferric. Ferrous and ferric ions are precipitated as iron carbonate and iron hydroxides in the following area containing carbonate buffer. The last functional layer contains printed pure A solution and B 1:10 diluted solution of BCA-test printed with a cylinder capable of transferring 24.9 ml/m$^2$ of ink. Violet colour occurs for 300 μg samples containing 0.5 g/l of sugar, demonstrating an ability to detect an amount of 150 μg of sugar such as fructose, saccharose, lactose, maltose or dextrin in fluid sample. However, test sensitivity decreases along with the sugar order given above and therefore even smaller sugar concentrations are detectable with the first mentioned sugars.

Figure 2:
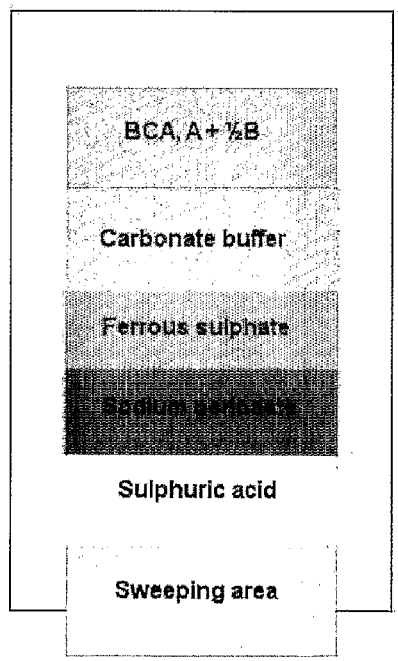
FIG. 2. Specific example of a fabric suitable for a sugar test showing reagents present in different fabric regions.

Orthoperiodic acid can be replaced by separate acid, for example weak sulphuric acid, and sodium periodate layers. Instead of ferrous sulphate, sodium thiosulphate can also be used for the inactivation of periodate as shown in FIG. 2.

The above concept of the moisture-absorbing fabric was also tested in a test tube. Using the reagents of this test embodiment, the chemicals were measured in a test tube in the order shown in Table 5.1. After ferrous sulphate was added, the solution became somewhat cloudy since trivalent ferric ions was formed in the solution. Ferrous and ferric carbonated and hydroxides were sedimented to the bottom of the test tube within five minutes following the addition of solution A included in the BCA mix.

TABLE 5.1

| BCA carbohydrate test functional at room temperature | |
|---|---|
| Reagent | Volume |
| Sugar solution 1 g/l | 1 ml |
| Periodic acid 11.3 g/l | 100 μl |
| Ferrous sulphate 72 g/l | 30 μl |
| BCA mix, solution B | 10 μl |
| BCA mix, solution A | 1 ml |

At a sugar concentration of 1 g/l, the solution immediately changed colour to violet. The colour continued to darken over time, which may be assumed to be due to the slow reduction of copper. At a sugar concentration of 0.01 g/l, the colour developing to a visually detectable level took seven minutes with mono- and disaccharides; the development was slow with dextrin and starch.

One advantage of the present invention and the related test was its processibility with roll-to-roll printing methods. For this reason, all of the chemicals used in the test can be transferred onto fabric by printing methods. Manufacturing the preferred test involves five chemicals being printed on a fabric successively. The fabric stretches during printing, which requires high-precision alignment capacity from the equipment. In addition, many reagents are colourless, which further complicates monitoring the print quality and aligning the different areas. According to the invention, printing is easiest with a press in which the number of print units corresponds to the number of reagents used. In this case the recommended number of print units is five for the preferred test. This kind of equipment makes it possible to print all chemicals onto the fabrics during one run. This reduces the impact of problems associated with aligning different chemical layers and stretching since the stretch would affect all print units identically.

The test developed under the invention is the first non-enzymatic test for sugar determination that functions at room temperature. The method is also capable of determining neutral sugars, which many tests fail to detect. Important insights provided by the invention are the chemical modification of the analyte e.g. the chemical modification of sugars with periodic acid, and inactivation of the interfering reagents before the indication step and the use of fabric. One embodiment of the invention provides a flexible test based on a moisture-absorbing fabric, which facilitates the precipitation of interfering chemicals on the fabric, thus stopping their further movement on the fabric.

The invention claimed is:

1. A test device for determining the presence or amount of a carbohydrate analyte in a sample said device comprising a synthetic fabric carrying a non-enzymatic means for chemically-modifying a carbohydrate analyte, a means for detecting said chemically-modified carbohydrate analyte at room temperature, and a means for inactivating an interfering agent, wherein said synthetic fabric is adapted for sequential movement of the sample through the synthetic fabric, the synthetic fabric comprising
   a chemical-modifying area comprising a means for chemically-modifying carbohydrate;
   an inactivation area comprising a means for inactivating an agent which interferes with the detection of chemically-modified carbohydrate; and
   an indication area comprising means for detecting chemically-modified carbohydrate.

2. A device according to claim 1 wherein the fabric is laminated with an impermeable layer and/or a layer material permitting one-way passage of sample or reagent.

3. A device according to claim 2 wherein the laminated impermeable layer comprises at least one opening.

4. A device according to claim 2 wherein the laminated layer permitting one-way flow of sample or reagent limits back-flow of sample or reagent to the sampled surface.

5. A device for determining the presence or amount of a carbohydrate analyte in a sample, said device comprising a layer of fabric material comprising periodic acid or sodium periodate as reagent for chemically modifying the carbohydrate and further comprising sodium thiosulphate or ferrous sulphate for neutralising said chemical modifying reagent prior to detecting the chemically-modified carbohydrate using a copper-complexing agent using bicinchoninic acid.

6. A device according to claim 1, wherein the carbohydrate analyte comprises a sugar.

7. A device according to claim 6, wherein the sugar comprises fructose, dextrin, lactose, maltose, or sucrose.

8. The test device of claim 1, wherein said device comprises a means for inactivating an interfering agent.

* * * * *